(12) United States Patent
Ostermaier

(10) Patent No.: US 8,815,186 B2
(45) Date of Patent: Aug. 26, 2014

(54) NICKEL COMPOSITIONS FOR PREPARING NICKEL METAL AND NICKEL COMPLEXES

(75) Inventor: John J. Ostermaier, Orange, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 176 days.

(21) Appl. No.: 12/968,373

(22) Filed: Dec. 15, 2010

(65) Prior Publication Data

US 2011/0311428 A1    Dec. 22, 2011

Related U.S. Application Data

(60) Provisional application No. 61/287,757, filed on Dec. 18, 2009, provisional application No. 61/380,445, filed on Sep. 7, 2010.

(51) Int. Cl.
  *C01G 1/00*    (2006.01)
(52) U.S. Cl.
  USPC ............ 423/144; 423/138; 423/140; 423/142
(58) Field of Classification Search
  USPC ................................. 423/138, 140, 142, 144
  See application file for complete search history.

(56) References Cited

U.S. PATENT DOCUMENTS

| | | | |
|---|---|---|---|
| 3,496,215 A | 2/1970 | Drinkard et al. | |
| 3,496,217 A | 2/1970 | Drinkard, Jr. et al. | |
| 3,631,191 A | 12/1971 | Kane et al. | |
| 3,655,723 A | 4/1972 | Drinkard, Jr. | |
| 3,766,237 A | 10/1973 | Chin et al. | |
| 3,846,461 A | 11/1974 | Shook, Jr. | |
| 3,847,959 A | 11/1974 | Shook, Jr. et al. | |
| 3,903,120 A | 9/1975 | Shook, Jr. et al. | |
| 4,416,825 A | 11/1983 | Ostermaier | |
| 4,749,801 A | 6/1988 | Beatty et al. | |
| 5,512,696 A | 4/1996 | Kreutzer et al. | |
| 5,723,641 A | 3/1998 | Tam et al. | |
| 6,069,267 A | 5/2000 | Tam | |
| 6,171,996 B1 | 1/2001 | Garner et al. | |
| 6,906,218 B2 * | 6/2005 | Allgeier et al. | ............... 558/430 |
| 2003/0100802 A1 | 5/2003 | Shapiro | |
| 2004/0106815 A1 | 6/2004 | Ritter | |

FOREIGN PATENT DOCUMENTS

| | | | |
|---|---|---|---|
| CN | 101478044 A | * | 7/2009 |
| CN | 101733106 | | 6/2010 |
| EP | 0985448 | | 3/2000 |
| GB | 146407 | | 11/1921 |
| GB | 255884 | | 4/1927 |
| GB | 703826 | | 2/1954 |
| JP | 03249943 A | * | 11/1991 |
| JP | 07005494 A | * | 1/1995 |
| JP | 2001-335326 | | 12/2001 |
| JP | 2001335326 A | * | 12/2001 |

OTHER PUBLICATIONS

Tolman et al., Advances in Catalysis, 1985, 33, pp. 1-46.
R. M. Mallya et al., The Journal of the Indian Institute of Science, 1961, vol. 43, Pt. I pp. 44-51, Pts. II, III, IV pp. 65-96, Pts. V, VI, VII pp. 131-157.
M. A. Rhamdhani et al., Metallurgical and Materials Transactions B2008, vol. 39B, pp. 218-233 and 234-245.
"CN101478044A—English Translation".
"JP2001335326A—English Translation".
"JP3249943A—English Translation".
"JP7005494A—English Translation".

* cited by examiner

*Primary Examiner* — Melvin C Mayes
*Assistant Examiner* — Melissa Stalder
(74) *Attorney, Agent, or Firm* — Robert B. Furr, Jr.

(57) ABSTRACT

Nickel compositions for use in manufacturing nickel metal compositions, and specifically to methods of making basic nickel carbonates used to produce nickel metal compositions are disclosed. By varying the molar ratios of carbonates and bicarbonates to nickel salts, the methods provide basic nickel carbonates that produce superior nickel-containing solids that react more effectively with phosphorous-containing ligands. The phosphorous containing ligands can be both monodentate and bidentate phosphorous-containing ligands.

19 Claims, No Drawings

NICKEL COMPOSITIONS FOR PREPARING NICKEL METAL AND NICKEL COMPLEXES

RELATED APPLICATIONS

This application claims benefit to U.S. Provisional Application No. 61/287,757 filed on Dec. 18, 2009 and U.S. Provisional Application No. 61/380,445 filed on Sep. 7, 2010, both herein incorporated by reference in their entirety.

FIELD OF THE INVENTION

The invention relates to nickel compositions for use in manufacturing nickel metal compositions, and specifically to methods of making basic nickel carbonates (BNC) used to produce nickel metal compositions. The nickel metal compositions can be used to produce nickel catalyst complexes with phosphorous-containing ligands.

BACKGROUND OF THE TECHNOLOGY

Hydrocyanation catalyst systems, particularly pertaining to the hydrocyanation of ethylenically unsaturated compounds, are known in the art. For example, systems useful for the hydrocyanation of 1,3-butadiene (BD) to form pentenenitrile (PN) and in the subsequent hydrocyanation of pentenenitrile to form adiponitrile (ADN) are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723 and 3,766,237, and Tolman et al., *Advances in Catalysis*, 1985, 33, 1. The hydrocyanation of activated ethylenically unsaturated compounds, such as with conjugated ethylenically unsaturated compounds (e.g., BD and styrene), and strained ethylenically unsaturated compounds (e.g., norbornene) proceeds without the use of a Lewis acid promoter, while hydrocyanation of unactivated ethylenically unsaturated compounds, such as 1-octene and 3-pentenenitrile (3PN), requires the use of a Lewis acid promoter. Recently, catalyst compositions and processes for the hydrocyanation of monoethylenically unsaturated compounds using zero-valent nickel and bidentate phosphite ligands in the presence of Lewis acid promoters have been described; for example in U.S. Pat. Nos. 5,512,696; 5,723,641 and 6,171,996.

U.S. Pat. No. 3,903,120 describes the preparation of zerovalent nickel complexes of the types $Ni(MZ_3)_4$ and $Ni(MZ_3)_2A$; wherein M is P, As or Sb; Z is R or OR, wherein R is an alkyl or aryl radical having up to 18 carbon atoms and may be the same or different, and at least one Z is OR; A is a monoolefinic compound having 2 to 20 carbon atoms; the R radicals of a given $MZ_3$ of $Ni(MZ_3)_2A$ preferably being so chosen that the ligand has a cone angle of at least 130°; are prepared by reacting elemental nickel with the monodentate $MZ_3$ ligand at a temperature in the range of 0° C.-150° C. in the presence of a halogen-containing derivative of the monodentate $MZ_3$ ligand as a catalyst. A more rapid reaction is realized by carrying out the preparation in an organonitrile solvent.

U.S. Pat. No. 4,416,825 also describes an improved, continuous process for the preparation of hydrocyanation catalysts comprising zerovalent nickel complexes with monodentate organophosphorus compounds (ligands) by controlling the temperature of the reaction relative to the amount of monodentate ligand and conducting the reaction in the presence of a chlorine ion and organic nitrile such as adiponitrile.

There are several processes that can be used to make nickel catalyst complexes with phosphorous-containing ligands. One method is a reaction between nickel bis(1,5-cyclooctadiene) $[NI(COD)_2]$ and a phosphite ligand; however, this process is not very economical because of the high costs of $Ni(COD)_2$. Another process involves the in situ reduction of anhydrous nickel chloride with zinc dust in the presence of the phosphite ligand. For this reaction to be successful, the nickel metal must react with the phosphorous-containing ligand at a sufficient rate to produce the nickel complex.

U.S. Pat. No. 6,171,996 describes zero-valent nickel complexes comprising bidentate phosphite ligands prepared or generated according to techniques well known in the art, as described, for example, in U.S. Pat. Nos. 3,496,217; 3,631,191; 3,846,461; 3,847,959 and 3,903,120. For example, divalent nickel compounds may be combined with a reducing agent, to serve as a source of zero-valent nickel in the reaction. Suitable divalent nickel compounds are said to include compounds of the formula $NiY_2$ where Y is halide, carboxylate, or acetylacetonate. Suitable reducing agents are said to include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120 is also a suitable source of zero-valent nickel.

In comparison to monodentate phosphorus-containing ligands, bidentate phosphorus-containing ligands generally react more slowly with nickel metals described in the above references. One example of a suitable nickel metal is the INCO type 123 nickel metal powder (Chemical Abstract Service registry number 7440-02-0), derived from the decomposition of nickel carbonyl at elevated temperatures.

Many nickel salts can be converted to nickel metal by reduction with hydrogen at elevated temperatures. Potential sources are nickel oxide, nickel formate, nickel oxalate, nickel hydroxide, nickel carbonate, and basic nickel carbonate (BNC). BNC production has been disclosed by R. M. Mallya, et al. in the *Journal of the Indian Institute of Science* 1961, Vol. 43, pages 44-157 and M. A. Rhamdhani, et al., *Metallurgical and Materials Transactions B* 2008, Vol. 39B, pages 218-233 and 234-245.

SUMMARY OF THE INVENTION

Bidentate ligands may be converted to nickel catalysts that have certain advantages over the nickel catalysts comprising monodentate ligands, especially as olefin hydrocyanation catalysts. Unfortunately, the INCO type 123 nickel metal powders have insufficient reactivity with the some of these bidentate ligands. Therefore, a nickel metal powder that is sufficiently reactive with bidentate phosphorous ligands and methods of making the nickel metal powder is desirable.

Basic nickel carbonate (BNC) is an inexpensive, commercially available, nickel source. However, evaluation of BNC samples from different mines and chemical vendors has revealed that different available BNC materials give rise to nickel metals with a wide range of reactivity with phosphorous-containing ligands to form nickel complexes.

The invention disclosed herein provides a basic nickel carbonate, which yields a nickel metal that is highly reactive with both monodentate and bidentate phosphorous-containing ligands in forming nickel metal complexes. Also disclosed are methods of making the basic nickel carbonate, since it has also been discovered that precipitation conditions for making the basic nickel carbonate influence the activity of the resulting nickel metal. The resulting nickel metal is useful in forming nickel metal complexes for producing pentenenitriles and dinitriles by hydrocyanation.

In one aspect, a method of making a nickel-containing composition is disclosed, comprising: (i) contacting a precipitant solution with a nickel solution in a precipitation reactor to form a reaction mixture; and (ii) precipitating said nickel-containing composition from said reaction mixture; wherein said nickel-containing solution comprises nickel(II) ions and water and said precipitant solution is selected from the group consisting of: (a) bicarbonate ions and water, (b) carbonate ions and water, and (c) mixtures thereof; and further wherein the mole ratio of bicarbonate ions to nickel ions in the reaction mixture is between 0:1 to 2:1 and said mole ratio of carbonate ions to nickel ions in the reaction mixture is between 0:1 to 1.6:1.

In a further aspect, the precipitant solution is added to the nickel solution, for example, by gradual addition.

DETAILED DESCRIPTION

Definitions

Monodentate: A single phosphorous atom that may bond to a single nickel atom to form the nickel complex.

Bidendate: Two phosphorous atoms that may bond to a single nickel atom to form the nickel complex.

Phosphite: An organophosphorous compound comprising a trivalent phosphorous atom bonded to three oxygen atoms.

Phosphonite: An organophosphorous compound comprising a trivalent phosphorous atom bonded to two oxygen atoms and one carbon atoms.

Phosphinite: An organophosphorous compound comprising a trivalent phosphorous atom bonded to one oxygen atoms and two carbon atoms.

Phosphine: An organophosphorous compounding comprising a trivalent phosphorous atom bonded to three carbon atoms.

Disclosed are novel nickel compositions, comprising nickel, and methods of making the same. The nickel compositions can be made by contacting a precipitant solution to a nickel solution in a precipitation reactor to form a reaction mixture; and (ii) precipitating said nickel composition from said reaction mixture, wherein said nickel solution comprises nickel(II) ions and water and said precipitant solution is selected from the group consisting of: (a) bicarbonate ions and water, (b) carbonate ions and water, and (c) mixtures thereof. The mole ratio of bicarbonate ions to nickel ions in the reaction mixture at the conclusion of said feeding can range from 0:1 to 2:1, including from about 0:1 to about 1.6:1, from about 0:1 to about 1.2:1, from about 1.0:0 to about 1.9:1, from about 1.2:1 to about 1.9:1, from about 0.8:1 to about 1.4:1, from about 1.0:1 to about 1.8:1, from about 1.0:1 to about 1.6:1, from about 1.0:1 to about 1.4:1, from about 0.8:1 to about 1.4:1, and from about 0.8:1 to about 1.2:1. The mole ratio of carbonate ions to nickel ions in the reaction mixture at the conclusion of said feeding can range from 0:1 to 1.6:1, including from about 0:1 to about 1.4:1, from about 1.0:0 to about 1.2:1, from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution. As detailed more fully below, the molar ratio has a surprising effect on the resulting nickel metal's effectiveness of reacting with the phosphorous ligands.

The precipitation reactor may be any suitable containment vessel such as a tank or pipe. Further, the reaction mixture may be agitated prior to and/or during the precipitation of the nickel composition. For example, agitation may be done by mechanical stirring, pumped circulation loop, flow-through static mixture, or ultrasound. The nickel composition may be precipitated within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. Furthermore, the nickel composition may be precipitated from the reaction mixture in the presence of added carbon dioxide. For example, the carbon dioxide can be added to the precipitation reactor, added to the nickel solution, added to the precipitant solution, or added to the reaction mixture, and any combination thereof. Also, the precipitant solution may be fed over a period of from about 30 minutes to about 60 minutes, and can be done in a semi-continuous or continuous manner. Further, the precipitant solution can be added to the nickel solution in the precipitation reactor in a semi-continuous or continuous manner, for example, gradual addition.

The reaction mixture may also be digested after contacting the precipitant solution to the nickel solution by heating the reaction mixture from between about 50° C. and about 90° C. for a period of from about 0.25 hours to about 24 hours. Other suitable temperature ranges include from about 60° C. to about 80° C. and from about 65° C. to about 75° C. Other suitable time periods can range from about 2 hours to about 24 hours, including from about 4 hours to about 20 hours, from about 6 hours to about 16 hours, and from about 8 hours to about 12 hours.

The disclosed nickel composition methods can further comprise, after the precipitation step, washing the precipitated nickel composition with water; and partially drying the precipitated nickel composition. For example, the precipitated nickel composition from the reaction mixture is separated from the reaction mixture by filtration or decantation, the resulting precipitated nickel composition is washed with water by filtration or decantation, and the resulting precipitated nickel composition is dried by water evaporation between 60° C. and 100° C. Drying can be performed under ambient pressure or under vacuum, and in the presence of an inert gas such as nitrogen.

The nickel solution, comprising nickel(II) ions and water, may be prepared by dissolving a nickel(II) salt in water. The nickel salt can be any salt that is soluble in water, for example $NiCl_2$, $NiSO_4$, and $Ni(NO_3)_2$. The precipitant solution, comprising bicarbonate ions, may be prepared by dissolving a bicarbonate salt, for example, $NaHCO_3$ and $NH_4HCO_3$, in water or prepared in-situ by dissolving $CO_2$ and an alkali metal hydroxide or ammonia in water by known methods. Likewise, the precipitant solution, comprising carbonate ions, may be prepared by dissolving a carbonate salt, for example $Na_2CO_3$ or prepared in-situ by dissolving $CO_2$ and an alkali metal hydroxide in water by known methods. The anion of the nickel salt and cation of the bicarbonate or carbonate salt may be selected such that a salt produced from the precipitation, comprising both the cation and anion from the reaction mixture (for example NaCl), is soluble in the water of the reaction mixture. Such a selection provides a method for separating said salt product from the precipitated nickel composition.

Also disclosed is a method of making a nickel-containing solid comprising nickel metal. The method comprises: (i) providing the nickel compositions disclosed above; and (ii) reducing at least a portion of the nickel composition of step (i) with a reducing agent to form a nickel-containing solid, comprising nickel metal, wherein said nickel-containing solid is adapted to effectively react with a bidendate phosphorous containing ligand to form a nickel complex of the phosphorous-containing ligand. The nickel-containing solid is more reactive with phosphorous-containing ligands than nickel-containing solids made by other processes, such as INCO type 123 nickel metal powder, nickel oxide, nickel formate, nickel oxalate, nickel hydroxide, nickel carbonate. The high reactivity is partially due to the BNC processes disclosed above, as well as the reducing process. The reducing agent can be hydrogen, carbon dioxide, carbon monoxide, methane, ammonia, hydrogen sulfide, merely to name a few nonlimiting examples of suitable reducing agents.

As previously stated, the amount of bicarbonate or carbonate ions fed relative to the nickel(II) ions charged greatly affects the reactivity of the resulting nickel-containing solid with the phosphorous-containing ligand to make a nickel complex. Because of the high costs of nickel, producers of BNC-type nickel compositions would be led to add excess amounts of the precipitant solution so as to recover as much of the nickel as economically feasible. However, it has been surprisingly found that the use of excess precipitant produces nickel metal of low reactivity for the phosphorous-ligand complex reaction. Highly reactive nickel is produced when reduced levels of precipitant are used, and presumably more of the nickel(II) ions are allowed to remain dissolved in the water of the resulting reaction mixture.

It has also been found that the precipitated nickel composition made using bicarbonate ions filters and washes much faster than the precipitated nickel composition made using carbonate ions. Also, the filtered precipitated nickel composition made using bicarbonate ions dries to a soft powder with little shrinkage. For these reasons, producing the nickel-containing solid using bicarbonate ions provides further desirable properties for downstream processing and handling of the dried precipitated nickel composition.

The reduction of the nickel composition with a reducing agent to form a nickel-containing solid may be performed at a temperature in the range from about 150° C. to about 700° C., including from about 300° C. to about 500° C., and from about 350° C. to about 450° C. In another aspect, the reduction temperature is from about 350° C. to about 1500° C., including from about 350° C. to about 450° C. The reduction pressure can range from about 0.01 atmospheres to about 100 atmospheres. Reduction may be carried out for a period of at least about 30 minutes using a stoichiometric excess of a reducing agent, such as hydrogen, even though one mole of hydrogen per mole of nickel composition is the theoretical and stoichiometric amount required for reduction. For example, the reducing period can be between about 1 to about 2 hours using a 2:1 mole ratio of hydrogen to nickel composition.

The disclosed nickel containing solids can be reacted with a phosphorous-containing ligand to make a nickel complex of the phosphorous-containing ligand. Such complexes are useful as a catalyst precursor for at least one of the following reactions: (1) reacting 1,3-butadiene with hydrogen cyanide to produce 2-methyl-3-butenenitrile and 3-pentenenitrile; (2) reacting 2-methyl-3-butenenitrile to produce 3-pentenenitrile; (3) reacting 3-pentenenitrile with hydrogen cyanide in the presence of a Lewis acid to produce adiponitrile; and (4) reaction 2-pentenenitrile with hydrogen cyanide in the presence of a Lewis acid to produce 3-pentenenitrile, 4-pentenenitrile, and adiponitrile.

The phosphorous-containing ligand may be a monodentate phosphite, monodentate phosphonite, monodentate phosphinite, monodentate phosphine, bidentate phosphite, bidentate phosphonite, bidentate phosphinite, or bidentate phosphine, and any combination of these members. Further, the phosphorous-containing ligand may be a monodentate phosphite to form the nickel complex of the monodentate phosphite then the nickel complex of the monodentate phosphite may be combined with a bidentate phosphorous-containing ligand. Likewise, the phosphorous-containing ligand may be a bidentate phosphite further comprising a monodentate phosphite.

When the phosphorous-containing ligand is a bidentate phosphite, the bidentate phosphite may be selected from the members of the groups consisting of Formula Ia, Formula Ib, Formula Ic, or any combination of these members:

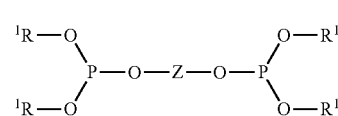

Formula Ia

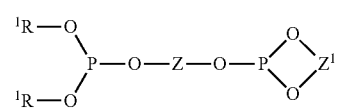

Formula Ib

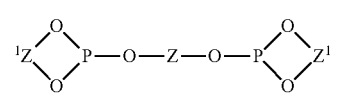

Formula Ic wherein in Formulae Ia, Ib, and Ic, $R^1$ is phenyl, unsubstituted or substituted with one or more $C_1$ to $C_{12}$ alkyl, $C_1$ to $C_{12}$ alkoxy groups, or groups of Formulae A and B, or —$(CH_2)_nOY^2$; or naphthyl, unsubstituted or substituted with one or more $C_1$ to $C_{12}$ alkyl or $C_1$ to $C_{12}$ alkoxy groups, or groups of Formulae A and B, or —$(CH_2)_nOY^2$; or 5,6,7,8-tetrahydro-1-naphthyl;

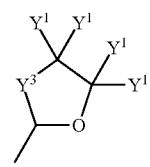

Formula A

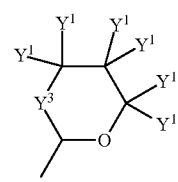

Formula B wherein in Formulae A and B, $Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4;

wherein in Formulae Ia, Ib, and Ic,

O—Z—O and O—$Z^1$—O are independently selected from the group consisting of structural Formulae II, III, IV, V, and VI:

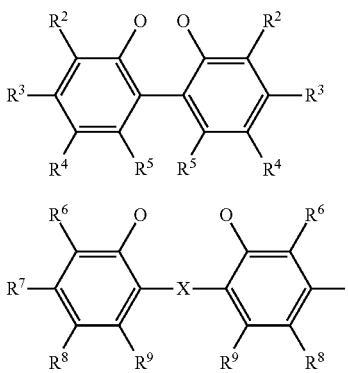

II

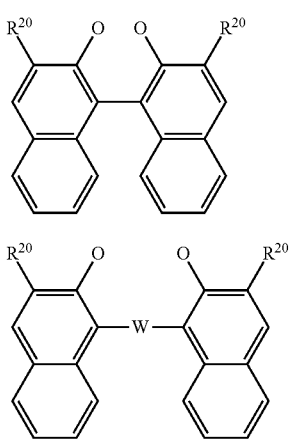

III wherein in Formulae II and III,
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or $CH(R^{10})$;
$R^{10}$ is H or $C_1$ to $C_{12}$ alkyl;

IV

V wherein in Formulae IV and V,
$R^{20}$ and $R^{30}$ are independently selected from the group consisting of H, $C_1$ to $C_{12}$ alkyl, and $C_1$ to $C_{12}$ alkoxy, and $CO_2R^{13}$;
$R^{13}$ is $C_1$ to $C_{12}$ alkyl or $C_6$ to $C_{10}$ aryl, unsubstituted or substituted with $C_1$ to $C_4$ alkyl;
W is O, S, or $CH(R^{14})$;
$R^{14}$ is H or $C_1$ to $C_{12}$ alkyl;

VI

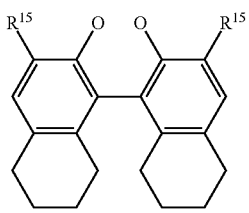

and wherein in Formulae VI,
$R^{15}$ is selected from the group consisting of H, $C_1$ to $C_{12}$ alkyl, and $C_1$ to $C_{12}$ alkoxy and
$CO_2R^{16}$; $R^{16}$ is $C_1$ to $C_{12}$ alkyl or $C_6$ to $C_{10}$ aryl, unsubstituted or substituted with $C_1$ to $C_4$ alkyl.

When the phosphorus-containing ligand is a bidentate phosphite, the bidentate phosphite may be selected from the group consisting of Formula VII and VIII, Formula VII

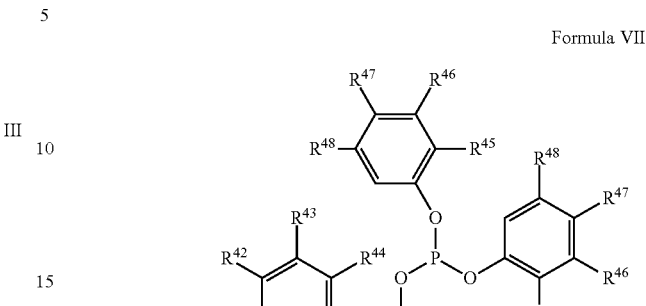
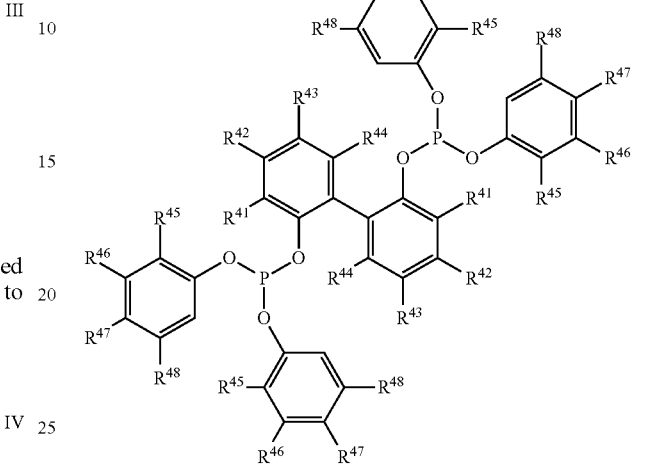

Formula VIII

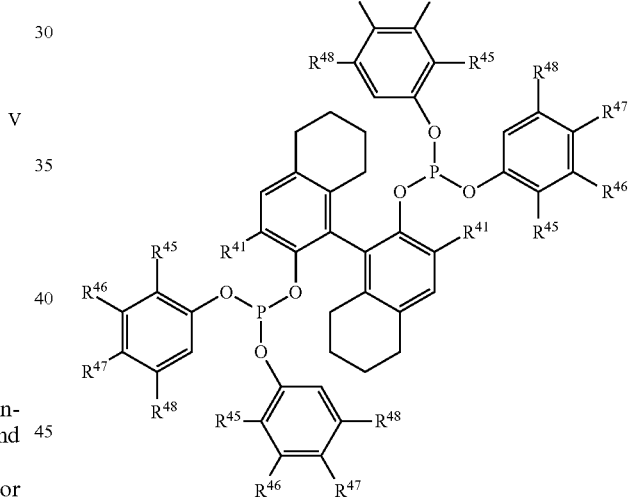

wherein,
$R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl;
or
wherein the phosphorus-containing ligand is a bidentate phosphite selected from the group consisting of Formula VII and VIII wherein,
$R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$, $R^{48}$ and are independently selected from the group consisting of H and $C_1$ to $C_4$ hydrocarbyl;
wherein the phosphorus-containing ligand is a bidentate phosphite selected from the group consisting of Formula VII and VIII wherein, $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;
or
$R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
wherein the phosphorus-containing ligand is a bidentate phosphite selected from the group consisting of Formula VII and VIII wherein,
$R^{41}$ is isopropyl or cyclopentyl;
$R^{45}$ is methyl or isopropyl; and
$R^{46}$, $R^{47}$, and $R^{48}$ are H;
and wherein the phosphorus-containing ligand is a bidentate phosphite selected from the group consisting of Formula VII and VIII wherein, $R^{41}$ is isopropyl; $R^{42}$, $R^{46}$, and $R^{48}$ are H; and $R^{43}$, $R^{44}$, $R^{45}$, and $R^{47}$ are methyl.

Furthermore, when the phosphorus-containing ligand is a bidentate phosphite, the bidentate phosphite may be selected from the group consisting of Formula IX

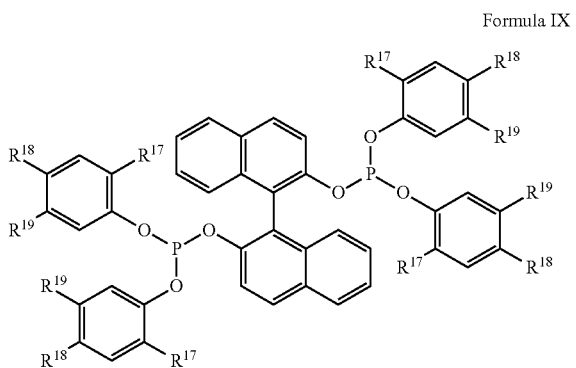

Formula IX wherein $R^{17}$ is isopropyl, $R^{18}$ is hydrogen, and $R^{19}$ is methyl; and Formula X

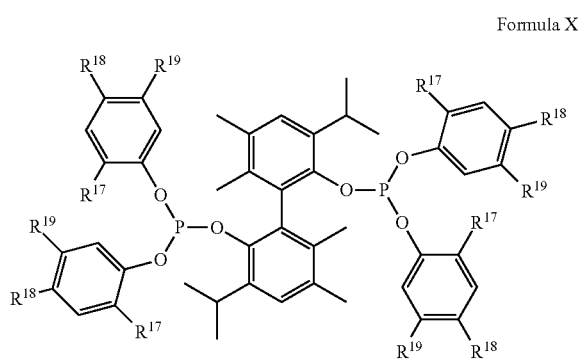

Formula X wherein $R^{17}$ is methyl, $R^{18}$ is methyl, and $R^{19}$ is hydrogen.

Additional bidentate ligands, ligand complexes, and methods of making the same, are disclosed in U.S. Pat. No. 6,171,996, herein incorporated by reference in its entirety.

In any preceding method comprising reacting the nickel-containing solid with a monodentate phosphorus-containing ligand, the reacting of the nickel-containing solid with the monodentate phosphorus-containing ligand may further comprise at least one halogenated catalyst comprising a phosphorus-halide bond selected from the group consisting of $PX_3$, $R^{17}PX_2$, $R^{18}OPX_2$, $[R^{19}][R^{20}]PX$, $[R^{21}][R^{22}O]PX$, and $[R^{23}O][R^{24}O]PX$;
wherein $R^{17}$, $R^{18}$, $R^{19}$, $R^{20}$, $R^{21}$, $R^{22}$, $R^{23}$, and $R^{24}$ are independently selected from the group consisting of $C_1$ to $C_{18}$ hydrocarbyl radicals and each X is a halide independently selected from the group consisting of chloride, bromide, and iodide The bidentate phosphorous containing ligands can further comprise at least one Lewis acid promoter. The Lewis acid may be selected from the group consisting of inorganic or organometallic compounds in which the cation is selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin. For example, the at least one Lewis acid is selected from the group consisting of zinc chloride, ferrous chloride, or a combination of zinc chloride and ferrous chloride.

The reaction between the nickel-containing solid and the phosphorous-containing ligand may further comprise an organonitrile selected from one or more members of the group consisting of 2-pentenenitrile, 3-pentenenitrile, 4-pentenenitrile, 2-methyl-3-butenenitrile, 2-methyl-2-byteneni-trile, adiponitrile, 2-methylglutaronitrile, and ethylsuccinot-rile.

Making the nickel complex or nickel complexes from the reaction of monodentate and bidentate ligands with the nickel-containing solids of this invention may be performed as described in U.S. Provisional application No. 61/287,757 and the following Examples. For example, a 5 wt % solution of a bidentate phosphorus-containing ligand in pentenenitrile solvent further comprising a Lewis acid like $ZnCl_2$ (0.5 to 2.5 moles Lewis acid per mole bidentate phosphorus-containing ligand) is contacted with the nickel-containing solid of the invention (for example, 4.0 wt % nickel-containing solid). Temperatures between 60° C. and 80° C. give acceptable reaction rates. Sufficient agitation may be used to suspend the nickel-containing solid in this reaction mixture.

EXAMPLES

Definitions of Abbreviations:
ADN=adiponitrile; BD=1,3-butadiene; hrs=hours; BNC=basic nickel carbonate; 2M3BN=2-methyl-3-butenenitrile; MGN=2-methylglutaronitrile; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile including both c3PN and t3PN unless specifically limited; 4PN=4-pentenenitrile; ppm=parts per million by weight; wt %=% by weight.

Various aspects of the disclosed BNC compositions, nickel-containing solids, phosphorous-containing nickel metal complexes, and methods of making the same may be further understood in view of the following non-limiting examples. In the following paragraphs, all references are incorporated herein by reference.

Bidentate Phosphorus-Containing Ligand

Examples 1 to 13 use a bidentate phosphite ligand, Ligand A. Ligand A may be prepared by any suitable synthetic means known in the art. For example, 3,3'-diisopropyl-5,5',6,6'-tetramethyl-2,2'-biphenol can be prepared by the procedure disclosed in U.S. Published patent application No. 2003/0100802 in which 4-methylthymol can undergo oxidative coupling to the substituted biphenol in the presence of a copper chlorohydroxide-TMEDA complex (TMEDA is N,N,N',N'-tetramethylethylenediamine) and air. The phosphorochloridite of 2,4-xylenol, [(CH$_3$)$_2$C$_6$H$_3$O]$_2$PCl, can be prepared, for example, by the procedure disclosed in U.S. Published patent application No. 2004/0106815. To selectively form this phosphorochloridite, anhydrous triethylamine and 2,4-xylenol can be added separately and concurrently in a controlled manner to PCl$_3$ dissolved in an appropriate solvent under temperature-controlled conditions. The reaction of this phosphorochloridite with the 3,3'-diisopropyl-5,5',6,6'-tetramethyl-2,2'-biphenol to form the desired Ligand A can be performed, for example, according to the method disclosed in U.S. Pat. No. 6,069,267, herein incorporated by reference. The phosphorochloridite can be reacted with 3,3'-diisopropyl-5,5',6,6'-tetramethyl-2,2'-biphenol in the presence of an organic base to form Ligand A, which can be isolated according to techniques well known in the art, for example as also described in U.S. Pat. No. 6,069,267. Ligand A is an example of a compound of Formula I and the Ligand A solutions in 3PN solvent below do not contain any halogenated catalysts of U.S. Pat. No. 3,903,120.

Ligand A

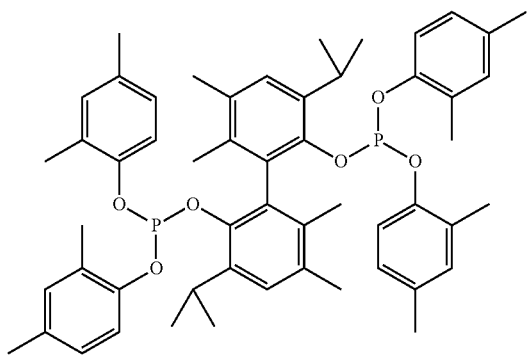

Example 16 uses a mixture of different monodentate phosphites, Ligand B, that is derived from the reaction of a m-cresol/p-cresol/phenol mixture with PCl$_3$. Ligand B is an example of a compound of Formula II.

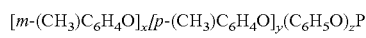

Ligand B wherein x+y+z=3.

Example 1

A 1 molar NiCl$_2$ solution (250 mL, 0.25 mole NiCl$_2$) in water is charged to a 1 liter beaker then this solution is magnetically stirred with heating to 70° C. While maintaining this temperature, a precipitant solution comprising bicarbonate ions (25.2 gm of NaHCO$_3$ dissolved in 400 mL water, 0.30 mole NaHCO$_3$) is fed continuously into the beaker at a rate of 10 mL/min as the reaction mixture is sparged with added CO$_2$ gas at a rate of 100 mL/min. At the conclusion of the precipitant solution addition, the total moles of bicarbonate ions fed per mole of nickel ions charged is 1.2:1. This addition causes a solid product, a BNC composition comprising nickel, to precipitate from the reaction mixture. After all the precipitant solution is added, the flow of carbon dioxide gas to the reaction mixture is then terminated and the resulting reaction mixture slurry is then allowed to digest for 2 hours at 70° C. At the conclusion of this digestion period, this slurry is then filtered using a sintered glass filter, and the solid filter cake is displacement washed with 200 mL water. The solid filter cake is then dried in a vacuum oven at 80° C. overnight while sweeping nitrogen through the vacuum oven.

Fifteen grams of the dried solid filter cake is then placed inside a reaction tube that can be heated within an electrical furnace located in a lab fume hood. Hydrogen gas flow to the reaction tube is then set at 0.2 liters/minute (about one atmosphere) with any hydrogen off gas from the reaction tube flowing through a bubbler. The temperature of the tube furnace is then increased at a rate of 10° C./minute to a final temperature of 400° C., and then held for one hour at 400° C., after which the reaction tube is allowed to cool under hydrogen flow. After the reaction tube temperature falls below 50° C. the flow to the reaction tube is switched to nitrogen gas to purge the hydrogen from the reaction tube. Valves on the reaction tube were then closed to prevent exposure of the resulting nickel-containing solid, comprising nickel metal, to air, and the entire reaction tube is transferred to a nitrogen-filled dry lab and the nickel-containing solid emptied into a bottle. This nickel-containing solid contains nickel metal as it is attracted to magnets. Exposing these nickel-containing solids to air can reduce rates for the following reaction and/or cause the nickel-containing solids to burn in air to form nickel oxide.

Nickel complexes are also prepared in this nitrogen-filled dry lab by placing 3.2 gm of this nickel-containing solid, 80 gm of a 5 wt % Ligand A solution in 3PN, and 0.50 gm of anhydrous ZnCl$_2$, into a bottle reactor that contained a magnetic stir bar. The nickel-containing solid is not soluble in this reaction mixture. With magnetic stirring, the reaction mixture is then heated rapidly to 80° C., and a filtered sample is withdrawn from this reaction mixture after 30 minutes and is found to contain 1460 ppm nickel, according to a UV-visible or LC analysis, as nickel complexes of Ligand A dissolved in the 3PN. For example, a calibrated absorption method that detects the soluble divalent nickel complex (Ligand A)Ni($\eta^3$-C$_4$H$_7$)C≡N—ZnCl$_2$ by the amount of absorption at a wavelength of 380 nanometers is used. This absorption method is calibrated against a LC analysis for total soluble nickel.

Examples 2 to 5

The general procedure of Example 1 is repeated in Examples 2 to 5, except that the total moles of bicarbonate ions fed per mole of nickel ions charged is varied from 1.6:1 to 2.0:1 by adjusting the amount of NaHCO$_3$ dissolved in the 400 mL water to prepare the precipitant solution. Results from the reaction of the resulting nickel-containing solids with the Ligand A solution and ZnCl$_2$ are provided in Table 1.

TABLE 1

Effect of the First Molar Ratio, Moles Bicarbonate Ions Fed/Mole Nickel Ions Charged, on the Reaction of the Resulting Nickel-Containing Solid with Ligand A and ZnCl$_2$ to Produce Nickel Complexes of Ligand A.

| | Precipitant Solution | | Moles HCO3 Ions Fed/Mole | |
|---|---|---|---|---|
| Example | gm NaHCO3 | mole NaHCO3 | Ni Ions Charged | ppm Ni* |
| 1 | 25.2 | 0.30 | 1.2 | 1460 |
| 2 | 33.6 | 0.40 | 1.6 | 1390 |
| 3 | 37.8 | 0.45 | 1.8 | 1060 |
| 4 | 39.3 | 0.47 | 1.9 | 823 |
| 5 | 42.0 | 0.50 | 2.0 | 92 |

*As nickel complexes of Ligand A dissolved in the 3PN.

Examples 1 through 5 illustrate that as the amount of bicarbonate ions fed is increased relative to the nickel ions charged, there is a decline in the reactivity of the resulting nickel-containing solid with a phosphorus-containing ligand to form soluble nickel complexes. That is, greater amounts of nickel complexes are formed when this first molar ratio, moles bicarbonate ions fed/mole nickel ions charged, is between 0.0:1 and 2.0:1.

Example 6

Example 2 is repeated except in the absence of sparging $CO_2$ gas through the reaction mixture during the feeding of the sodium bicarbonate solution to the 1 liter beaker comprising the nickel ions. As shown in Table 2, greater amounts of nickel complexes are formed from the reaction of the resulting nickel-containing solid with the Ligand A solution and $ZnCl_2$ when the solid product precipitates in the presence of added $CO_2$ gas.

TABLE 2

Effect of the Presence of Added $CO_2$ Gas During the Precipitation of the Solid Product on the Reaction of the Resulting Nickel-Containing Solid with Ligand A and $ZnCl_2$ to Produce Nickel Complexes of Ligand A.

| Example | Precipitant Solution gm NaHCO3 | mole NaHCO3 | Moles HCO3 Ions Fed/Mole Ni Ions Charged | ppm Ni* |
|---|---|---|---|---|
| 2 | 33.6 | 0.40 | 1.6 | 1390 |
| 6 | 33.6 | 0.40 | 1.6 | 965 |

*As nickel complexes of Ligand A dissolved in the 3PN.

Examples 7 and 8

Example 2 is repeated except that temperatures of the heated $NiCl_2$ solution, reaction mixture during continuous feeding of the precipitant solution to the 1 liter beaker, and digestion period are 50° C. for Example 7 and 90° C. for Example 8. In comparison to Example 2 (see Table 3), greater amounts of nickel complexes are formed from the reaction of the resulting nickel-containing solid with the Ligand A solution and $ZnCl_2$ when the solid product precipitates at 70° C. rather than 50° C. or 90° C.

TABLE 3

Effect of Precipitation Temperature on the Reaction of the Resulting Nickel-Containing Solid with Ligand A and $ZnCl_2$ to Produce Nickel Complexes of Ligand A.

| Example | Heated $NiCl_2$ Solution | Reaction Mixture | Digestion Period | ppm Ni* |
|---|---|---|---|---|
| 2 | 70° C. | 70° C. | 70° C. | 1390 |
| 7 | 50° C. | 50° C. | 50° C. | 845 |
| 8 | 90° C. | 90° C. | 90° C. | 850 |

*As nickel complexes of Ligand A dissolved in the 3PN according to an analysis.

Example 9

Example 2 is repeated except substituting $NiSO_4$ for $NiCl_2$. That is, continuously feeding the precipitant solution of Example 2 to a 1 molar $NiSO_4$ solution (250 mL, 0.25 mole $NiSO_4$) in water at 70° C. Similar to solid product precipitated from $NiCl_2$, equivalent amounts of nickel complexes are formed (1465 ppm nickel) after 30 minutes from the reaction of the resulting nickel-containing solid with the Ligand A solution and $ZnCl_2$ when the solid product precipitates from the $NiSO_4$ solution.

Example 10

A 1 molar $NiSO_4$ solution (250 mL, 0.25 mole $NiSO_4$) in water is charged to a 1 liter beaker then this solution is magnetically stirred with heating to 70° C. While maintaining this temperature, a precipitant solution comprising carbonate ions (21.2 gm of $Na_2CO_3$ dissolved in 400 mL water, 0.20 mole $Na_2CO_3$) is fed continuously into the beaker at a rate of 10 mL/min but no $CO_2$ gas is sparged into the reaction mixture. At the conclusion of the precipitant solution addition, the total moles of carbonate ions fed per mole of nickel ions charged is 0.8. This addition also causes a solid product to precipitate from the reaction mixture. After all the precipitant solution is added, the resulting reaction mixture slurry is then allowed to digest for 2 hours at 70° C. At the conclusion of this digestion period, this slurry is then filtered using a sintered glass filter, and the solid filter cake is displacement washed with 200 mL water. The solid filter cake is then dried in a vacuum oven at 80° C. while sweeping nitrogen through the vacuum oven overnight.

Fifteen grams of the dried solid filter cake is reduced with hydrogen flow at elevated temperatures as described in Example 1. Nickel complexes are also prepared as described in Example 1. A filtered sample is withdrawn from the reaction mixture in the bottle reactor after 30 minutes and is found to contain 1420 ppm nickel, according to a UV-Visible or LC analysis, as nickel complexes of Ligand A dissolved in the 3PN.

Examples 11 to 13

The general procedure of Example 10 is repeated in Examples 11 to 13. The difference being that the total moles of carbonate ions fed per mole of nickel ions charged is varied from 1.0:1 to 1.6:1 by adjusting the amount of $Na_2CO_3$ dissolved in the 400 mL water to prepare the precipitant solution. Results from the reaction of the resulting nickel-containing solids with the Ligand A solution and $ZnCl_2$ are provided in Table 4.

TABLE 4

Effect of the Second Molar Ratio, Moles Carbonate Ions Fed/Mole Nickel Ions Charged, on the Reaction of the Resulting Nickel-Containing Solid with Ligand A and $ZnCl_2$ to Produce Nickel Complexes of Ligand A.

| Example | Precipitant Solution gm Na2CO3 | mole Na2CO3 | Moles CO3 Ions Fed/Mole Ni Ions Charged | ppm Ni* |
|---|---|---|---|---|
| 10 | 21.2 | 0.20 | 0.8 | 1420 |
| 11 | 26.5 | 0.25 | 1.0 | 1340 |
| 12 | 31.8 | 0.30 | 1.2 | 1065 |
| 13 | 42.0 | 0.40 | 1.6 | 0 |

*As nickel complexes of Ligand A dissolved in the 3PN.

Examples 10 through 13 illustrate that the reactivity of the resulting nickel-containing solid with a phosphorus-containing ligand to form soluble nickel complexes can decline as the amount of carbonate ions fed is increased relative to the nickel ions charged. That is, greater amounts of nickel complexes are formed when this second molar ratio, moles carbonate ions fed/mole nickel ions charged, is between 0.0:1 and 1.6:1.

Example 14

Example 5 is repeated except that the order of addition is reversed for the solid precipitation reaction in the 1 liter beaker. That is, the 1 molar $NiCl_2$ solution is added to the precipitant solution to precipitate a solid product. After digestion, filtration, displacement washing, drying, reducing with hydrogen gas in the reactor tube at 400° C., followed by reacting the resulting nickel-containing solid with the Ligand A solution in 3PN and $ZnCl_2$, the filtered sample withdrawn from the reaction mixture is found to contain 0 ppm nickel as nickel complexes of Ligand A dissolved in the 3PN.

Example 15

At a constant precipitation temperature, the weight of the dried solid filter cake is also a function of the total moles of bicarbonate (Examples 1 to 9, Table 5) or carbonate ions (Examples 10 to 13, Table 6) fed per mole of nickel ions charged.

TABLE 5

Effect of the First Molar Ratio, Moles Bicarbonate Ions Fed/Mole Nickel Ions Charged, on the Weight of the Dried Solid Filter Cake and Reaction of the Resulting Nickel-Containing Solid with Ligand A and $ZnCl_2$ to Produce Nickel Complexes of Ligand A.

| Example | 1 | 2 | 6 | 7 | 8 | 9 | 3 | 4 | 5 | 14 |
|---|---|---|---|---|---|---|---|---|---|---|
| Precipiating Temperature | 70° C. | 70° C. | 70° C. | 50° C. | 90° C. | 70° C. | 70° C. | 70° C. | 70° C. | 70° C. |
| Moles HCO3 Ions Fed/Mole Ni Ions Charged | 1.2 | 1.6 | 1.6 | 1.6 | 1.6 | 1.6 | 1.8 | 1.9 | 2.0 | 2.0 |
| gm Dried Solid Filter Cake | 16.2 | 21.70 | 22.1 | 22.3 | 15.9 | 23.5 | 24.2 | 26.8 | 27.6 | 26.2 |
| ppm Ni* | 1460 | 1390 | 965 | 845 | 850 | 1465 | 1060 | 823 | 92 | 0 |

TABLE 6

Effect of the Second Molar Ratio, Moles Carbonate Ions Fed/Mole Nickel Ions Charged, on the Weight of the Dried Solid Filter Cake and Reaction of the Resulting Nickel-Containing Solid with Ligand A and $ZnCl_2$ to Produce Nickel Complexes of Ligand A.

| | Example | | | |
|---|---|---|---|---|
| | 10 | 11 | 12 | 13 |
| Moles CO3 Ions Fed/Mole Ni Ions Charged | 0.8 | 1.00 | 1.2 | 1.6 |
| gm Dried Solid Filter Cake | 23.6 | 26.70 | 28.7 | 32.7 |
| ppm Ni* | 1420 | 1340 | 1065 | 0 |

*As nickel complexes of Ligand A dissolved in the 3PN.

Also, it is generally observed that times required for the filtration of the precipitated solid product and displacement wash of the solid filter cake, as described in Examples 1 to 14, are greater when the solid product is precipitated using carbonate ions in comparison to using bicarbonate ions. For example at equivalent filtration conditions, the filtration time is 14 minutes and the displacement wash time is 40 minutes for the solid product of Example 11 that is precipitated with carbonate ions. But for the solid product precipitated with bicarbonate ions, the filtration time and displacement wash time can both be less than 1 minute each.

Example 16

The nickel-containing solids of Examples 1 to 13 are reacted with the monodentate phosphite Ligand B in 3PN solvent to form nickel complexes, comprising zero-valent nickel and Ligand B, in the absence of a Lewis acid such as $ZnCl_2$.

Example 17

$ZnCl_2$ is at least partially separated from the nickel complex of Examples 1 to 12 then the nickel complex of Ligand A contacts BD and HC≡N in a reaction zone. A catalyst forms to produce 3PN, 2M3BN, or a combination thereof. The same nickel complexes also react with 2M3BN to produce 3PN.

Nickel complexes of Ligand B of Example 16 contact HC≡N and BD in a reaction zone. A catalyst forms to produce 3PN, 2M3BN, or a combination thereof. The same nickel complexes also react with 2M3BN to produce 3PN.

In the presence of a Lewis acid promoter, like $ZnCl_2$, the soluble nickel complexes of Ligand A from bottle reactors of Examples 1 to 12 contact HC≡N and 3PN in a reaction zone. A catalyst forms converting greater than 90% of the 3PN to dinitriles comprising ADN, MGN, and ESN, with an ADN distribution of 95-96%. The ADN distribution equals 100%*wt % ADN/(wt % ADN+wt % MGN+wt % ESN), as determined by gas chromatography (GC).

In the presence of a Lewis acid promoter, like $ZnCl_2$, the soluble nickel complexes of Ligand A from bottle reactors of Examples 1 to 12 contact HC≡N and 2PN in a reaction zone. A catalyst forms converting a portion of the 2PN to 3PN, 4PN, and ADN.

In the presence of a Lewis acid promoter, like $ZnCl_2$, triphenylboron, or compounds of the chemical formula [Ni$(C_4H_7C$≡$N)_6$][$(C_6H_5)_3BC$≡$NB(C_6H_5)_3]_2$ as disclosed in U.S. Pat. No. 4,749,801, the nickel complexes of Example 16 contact HC≡N and 3PN in a reaction zone. A catalyst forms converting 3PN to dinitriles comprising ADN, MGN, and ESN, wherein ADN is the major dinitrile product.

The invention has been described above with reference to the various aspects of the disclosed nickel compositions, basic nickel carbonates, and methods of making the same. Obvious modifications and alterations will occur to others upon reading and understanding the proceeding detailed description. It is intended that the invention be construed as including all such modifications and alterations insofar as they come within the scope of the claims.

What is claimed is:

1. A method of making an organic-soluble complex of nickel metal with a phosphorus-containing ligand, the method comprising
   a. contacting a precipitant solution with a nickel solution in a precipitation reactor to form a reaction mixture, wherein the precipitant solution is added to the nickel solution in the precipitation reactor in a semi-continuous or continuous manner; and
   b. precipitating a nickel-containing composition comprising nickel ions from said reaction mixture; wherein said nickel solution comprises nickel(II) ions and water and said precipitant solution is selected from the group consisting of: (i) bicarbonate ions and water, (ii) carbonate ions and water, and (c) mixtures thereof; and further wherein the mole ratio of bicarbonate ions to nickel ions in the reaction mixture is between 0.8:1 and 1.8:1 and said mole ratio of carbonate ions to nickel ions in the reaction mixture is between 0.8:1 and 1.6:1, to provide the nickel-containing composition;

the method further comprising c. then, reducing the nickel-containing composition to nickel metal with a reducing agent, optionally at an elevated temperature; then, d. contacting the nickel metal and a phosphorus-containing ligand, to provide an organic-soluble nickel-ligand complex suitable as a catalyst for a hydrocyanation reaction.

2. The method of claim 1, wherein said nickel(II) ions are selected from the group consisting of: $NiCl_2$, $NiSO_4$, and $Ni(NO_3)_2$.

3. The method of claim 2, wherein said nickel(II) ions are $NiCl_2$.

4. The method of claim 1, wherein said bicarbonate ions are selected from the group consisting of: $NaHCO_3$ and $NH_4HCO_3$.

5. The method of claim 1, wherein said carbonate ions are from $Na_2CO_3$.

6. The method of claim 1, further comprising contacting said reaction mixture with carbon dioxide.

7. The method of claim 6, wherein said contacting is performed while precipitating said nickel composition.

8. The method of one of claims 1, 2, or 3, further comprising digesting the reaction mixture after precipitating said nickel composition.

9. The method of claim 8, wherein said digestion is performed at a temperature from about 50° C. to about 90° C. and a duration from about 0.25 hours to about 24 hours.

10. The method of one of claims 1, 2, or 3, wherein said precipitating said nickel composition is performed at a temperature of from about 0° C. to about 90° C.

11. The method of claim 10, wherein said temperature is from about 50° C. to about 90° C.

12. The method of claim 11, wherein said temperature is from about 65° C. to about 75° C.

13. The method of one of claims 1, 2, or 3, wherein said mole ratio of bicarbonate ions to nickel ions can be selected from the group consisting of: from about 0.8:1 to about 1.4:1, from about 1.0:1 to about 1.8:1, from about 1.0:1 to about 1.6:1, from about 1.0:1 to about 1.4:1, from about 0.8:1 to about 1.4:1, and from about 0.8:1 to about 1.2:1.

14. The method of one of claims 1, 2, or 3, wherein said mole ratio of carbonate ions to nickel ions can be selected from the group consisting of: from about from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1.

15. The method of claim 13, wherein said bicarbonate ions are selected from the group consisting of: $NaHCO_3$ and $NH_4HCO_3$.

16. The method of claim 1, wherein said carbonate ions are from $Na_2CO_3$.

17. The method of one of claims 1, 2, or 3 further comprising (c) washing said nickel composition with water; and (d) partially drying the precipitated nickel composition.

18. The method of claim 1 wherein the reducing agent comprises hydrogen, carbon monoxide, or methane.

19. The method of claim 1, wherein the phosphorus-containing ligand is a monodentate phosphite, mondentate phosphonite, monodentate phosphinite, monodentate phosphine, bidentate phosphite, bidentate phosphonite, bidentate phosphinite, or bidentate phosphine, or any combination thereof.

* * * * *